(12) United States Patent
Kobira et al.

(10) Patent No.: US 6,489,301 B1
(45) Date of Patent: Dec. 3, 2002

(54) SOLID PHARMACEUTICAL PREPARATION FOR DIALYSIS AND A PROCESS FOR PRODUCING THE SAME

(75) Inventors: Seigo Kobira, Osaka (JP); Kazuyoshi Harada, Osaka (JP)

(73) Assignee: Nipro Corporation, Osaka (JP)

( * ) Notice: Subject to any disclaimer, the term of this patent is extended or adjusted under 35 U.S.C. 154(b) by 218 days.

(21) Appl. No.: 09/587,982

(22) Filed: Jun. 6, 2000

(30) Foreign Application Priority Data

Jun. 7, 1999 (JP) .......................................... 11-158951

(51) Int. Cl.⁷ ...................... A01N 43/04; A61K 31/70
(52) U.S. Cl. ............................ 514/23; 514/25; 536/4.1; 536/18.5; 536/124
(58) Field of Search ...................... 514/23, 25; 536/4.1, 536/18.5, 124

(56) References Cited

U.S. PATENT DOCUMENTS

| | | | | |
|---|---|---|---|---|
| 4,415,547 A | * | 11/1983 | Yu et al. ........................ | 424/19 |
| 5,540,842 A | | 7/1996 | Aoyama et al. ............. | 210/647 |
| 5,912,398 A | * | 6/1999 | Goldstein et al. ................ | 71/6 |

FOREIGN PATENT DOCUMENTS

| | | |
|---|---|---|
| EP | 0 287 978 B1 | 4/1988 |
| EP | 0 567 452 B1 | 5/1996 |
| JP | 64-25725 A | 1/1989 |
| JP | 3-66621 A | 3/1991 |
| JP | 6-335527 A | 12/1994 |
| JP | 8-92071 A | 4/1996 |
| JP | 08/169836 A * | 7/1996 |
| JP | 8-169836 A | 7/1996 |
| JP | 08-169836 A | 7/1996 |
| JP | 10-259133 A | 9/1998 |
| JP | 10-330270 A | 12/1998 |
| JP | 11-114054 A | 4/1999 |

OTHER PUBLICATIONS

Database WP1 Week 9636, Derwent Publications Ltd., London, GB; AN 1996–358473, XP002173386 & JP 08 169836 A (Morishita Roussel KK), Jul. 2, 1996.

* cited by examiner

Primary Examiner—James O. Wilson
Assistant Examiner—Patrick Lewis
(74) Attorney, Agent, or Firm—Kubovcik & Kubovcik

(57) ABSTRACT

There is provided a solid pharmaceutical preparation for dialysis consisting of one composition, which is excellent in uniformity of the ingredients contained therein, is capable of preventing not only a reaction between sodium bicarbonate and a solid organic acid or between sodium bicarbonate and electrolytes but also a reaction between a solid organic acid and sodium acetate, and does not require further pulverization of the respective ingredients in the dialysis composition. The solid pharmaceutical preparation for dialysis containing an electrolyte for hemodialysis, a solid organic acid and glucose is characterized by a plurality of layers separated from each other on the surface of a nucleating particle of sodium chloride, wherein the plurality of separated layers include a layer (A) comprising sodium acetate but not containing the solid organic acid, a layer (B) comprising the solid organic acid but not containing sodium acetate, and a layer (C) comprising sodium bicarbonate.

12 Claims, 5 Drawing Sheets

SOLID PHARMACEUTICAL PREPARATION FOR DIALYSIS AND A PROCESS FOR PRODUCING THE SAME

FIELD OF THE INVENTION

The present invention relates to a solid pharmaceutical preparation for dialysis and, more particularly, to a solid dialysate concentrate for preparing a dialysis solution containing sodium hydrogencarbonate and a process for producing the same.

BACKGROUND OF THE INVENTION

When hemodialysis is carried out for a patient suffering from weakened hepatic function, the blood of the patient is cleaned in an artificial kidney. Generally, a dialysis solution is perfused in this artificial kidney and contacted via a dialysis membrane with the blood of the patient so that wastes in the blood are transferred to the dialysis solution. As this dialysis solution, an acetate dialysis solution has been used widely but has recently been substituted with a dialysis solution containing sodium hydrogencarbonate (i.e., sodium bicarbonate) drastically reducing unpleasant symptoms during dialysis.

The dialysis solution containing sodium bicarbonate is usually prepared from two kinds of dialysis solution, that is, a pharmaceutical preparation (referred to hereinafter as composition A) containing electrolytes (e.g. sodium chloride, potassium chloride, calcium chloride, magnesium chloride, and sodium acetate) and a pH adjusting agent (e.g., acetic acid) and a pharmaceutical preparation (referred to hereinafter as composition B) containing sodium bicarbonate. These dialysis solutions may contain sugars such as glucose or may be mixed with another pharmaceutical preparation containing sugars.

Heretofore, compositions A and B were commercialized in the form of a concentrated solution prepared at a predetermined concentration and used by the customer after being diluted with water. However, about 300 L perfusion solution of sodium hydrogencarbonate is necessary for the dialysis of one patient, and thus in conducting dialysis treatment of a large number of patients, a large quantity of the concentrated solution must be used and diluted with water. Accordingly, there are recently many cases where composition B prepared in a powdery form is used to reduce the burden on those who prepare the dialysis solution and to reduce storage space. In this connection, a pharmaceutical preparation for dialysis consisting of two pulverized compositions, one of which is a pulverized composition A and the other of which is pulverized composition B, and a solid pharmaceutical preparation for dialysis consisting of all ingredients necessary for dialysis as one composition, namely a granulated or powdered solid dialysate concentrate, have also been developed.

As the one composition type of solid pharmaceutical preparation for dialysis, there are disclosed those obtained by mixing all ingredients necessary for a dialysis solution in the form of granules or powders, or by coating essential ingredients on a nucleating particle (Japanese Patent No. 2846883, Japanese Patent No. 2739898 and JP-A 10-259133). However, these pharmaceutical preparations suffer from the problem that since sodium bicarbonate, calcium salt and magnesium salt are directly contacted with one another, these ingredients react with crystallization water contained in the calcium salt and magnesium salt, or with moisture in the air, to form sparingly soluble salts. In addition, there is another problem that since sodium bicarbonate and acetic acid are directly contacted with each other, these ingredients react with each other to generate carbon dioxide, with the result that the pH of the dialysis solution can not be maintained in a suitable range (Japanese Patent No. 2846883 and Japanese Patent No. 2739898).

On one hand, a solid pharmaceutical preparation for dialysis comprising sodium bicarbonate in an innermost layer and sodium diacetate as an acid in an outermost layer (JP-A 10-259133) may generate carbon dioxide upon decomposition of sodium bicarbonate in the innermost layer by heat or water added in later steps. Further, the water and heat generated from the decomposition of sodium bicarbonate cause decomposition of glucose in the solid pharmaceutical preparation for dialysis. Moreover, acetic acid which has been bound to sodium acetate in sodium diacetate is easily released therefrom, and this acetic acid reacts with sodium bicarbonate to generate carbon dioxide and then the pH of the dialysis solution can not be maintained in a suitable range.

In consideration of these disadvantages, some solid pharmaceutical preparations for dialysis consisting of all ingredients necessary for dialysis as one composition are developed. In one pharmaceutical preparation, sodium bicarbonate and an organic acid, or sodium bicarbonate and calcium salt or magnesium salt are layered such that both of them are not contacted with each other and reaction therebetween is prevented (JP-A 6-335527, JP-A 8-169836, JP-A 8-92071 and JP-A 11-114054). Another solid pharmaceutical preparation for dialysis consisting of all ingredients necessary for dialysis as one composition is produced by granulating calcium salt, magnesium salt and solid organic acid together, but separately granulating sodium bicarbonate, and then mixing the above granulated ingredients and the granulated sodium bicarbonate (JP-A 6-335528 and JP-A 8-92070).

In these solid pharmaceutical preparations for dialysis, however, it is likely that if pH adjusting agents, i.e., a solid organic acid, and sodium acetate are contacted with each other, the solid organic acid reacts with sodium acetate to form free acetic acid, and the vaporized acetic acid reacts with sodium bicarbonate to generate carbon dioxide. Further, the respective ingredients to be coated on nucleating particles of electrolytes in the solid pharmaceutical preparations for dialysis must be finely pulverized by a sample mill and as a result, not only the steps but also the time for producing the preparation are increased. Additionally, a solid pharmaceutical preparation for dialysis having an outermost layer, which under drying and by spraying with water or an aqueous solution, has been coated with a fine powder obtained by pulverizing a mixture of sodium bicarbonate, sodium chloride and other electrolytes (JP-A 11-114054), contains a large amount of the powder and requires a longer time for coating and drying thereof such that the sodium bicarbonate may be decomposed by prolonged heating.

In addition, there is also known a solid pharmaceutical preparation for dialysis consisting of all ingredients prepared by mixing calcium salt, magnesium salt, solid organic acid, sodium bicarbonate and glucose coated respectively with sodium citrate (JP-A 10-87478), or a solid pharmaceutical preparation for dialysis consisting of all ingredients prepared by mixing calcium salt, magnesium salt, solid organic acid and sodium bicarbonate coated respectively with sodium chloride and/or potassium chloride (JP-A 10-330270). However, it is difficult to attain uniformity of the ingredients in the solid pharmaceutical preparations for dialysis because the solid organic acid as an ingredient added in a small amount, the calcium salt and magnesium salt are respectively mixed in the form of powder.

SUMMARY OF THE INVENTION

Under these circumstances as described above, the object of the present invention is to provide a solid pharmaceutical preparation for dialysis consisting of all ingredients as one composition, which is excellent in the uniformity of the ingredients therein, is capable of preventing not only a reaction between sodium bicarbonate and a solid organic acid, or sodium bicarbonate and electrolytes, but also a reaction between a solid organic acid and sodium acetate, and does not require further pulverization of the ingredients.

As a result of their eager study for solving the problems described above, the present inventors have found that a solid pharmaceutical preparation for dialysis which comprises a granule or powder with a plurality of layers of sodium acetate, solid organic acid and sodium bicarbonate separated respectively and preferably, which are coated with glucose and sodium bicarbonate in the form of non-pulverized crystals therein, achieves the intended object, thus arriving at the present invention.

That is, the present invention relates to a solid pharmaceutical preparation for dialysis comprising an electrolyte for hemodialysis, a solid organic acid and glucose and is characterized by comprising a plurality of layers which are separated from each other on the surface of a nucleating particle consisting of sodium chloride, wherein the plurality of layers include a layer (A) comprising sodium acetate but not containing the solid organic acid, a layer (B) comprising the solid organic acid but not containing sodium acetate, and a layer (C) comprising sodium bicarbonate.

Further, the present invention relates to a process for producing a pharmaceutical preparation for dialysis, which comprises forming a layer (A) containing sodium acetate but not containing solid organic acid on the surface of a nucleating particle, and forming a layer (B) containing solid organic acid and separated from the layer (A) on the surface of the nucleating particle, and forming a layer (C) containing sodium bicarbonate and separated from the layer (B) on the surface of the nucleating particle in this order.

In one embodiment of the present invention, the solid pharmaceutical preparation for dialysis comprises a nucleating particle consisting of sodium chloride, a first layer formed on said nucleating particles and containing sodium acetate but not containing a solid organic acid as layer (A), a second layer containing at least one compound selected from the group consisting of calcium chloride, magnesium chloride, potassium chloride and sodium chloride but not containing sodium acetate or a solid organic acid, a third layer containing a solid organic acid but not containing sodium acetate as layer (B), a fourth layer containing glucose powder and a fifth layer containing sodium bicarbonate powder as layer (C) in this order.

One embodiment of the process in the present invention comprises, (a) spraying an aqueous solution containing sodium acetate but not containing a solid organic acid on the surface of nucleating particles consisting of sodium chloride, and drying the particles, (b) spraying the particles obtained in step (a) with an aqueous solution containing at least one compound selected from the group consisting of calcium chloride, magnesium chloride, potassium chloride and sodium chloride but not containing sodium acetate and not containing a solid organic acid, and drying the particles, (c) spraying the particles obtained in step (b) with an aqueous solution containing a solid organic acid and not containing sodium acetate and drying the particles, (d) mixing glucose powder with the particles obtained in step (c), then spraying the particles with an aqueous solution containing glucose and/or sodium chloride and drying the particles, (e) mixing sodium bicarbonate powder with the particles obtained in step (d), then spraying the particles with an aqueous solution containing glucose and/or sodium chloride and drying the particles.

EMBODIMENT OF THE INVENTION

Figure 1:
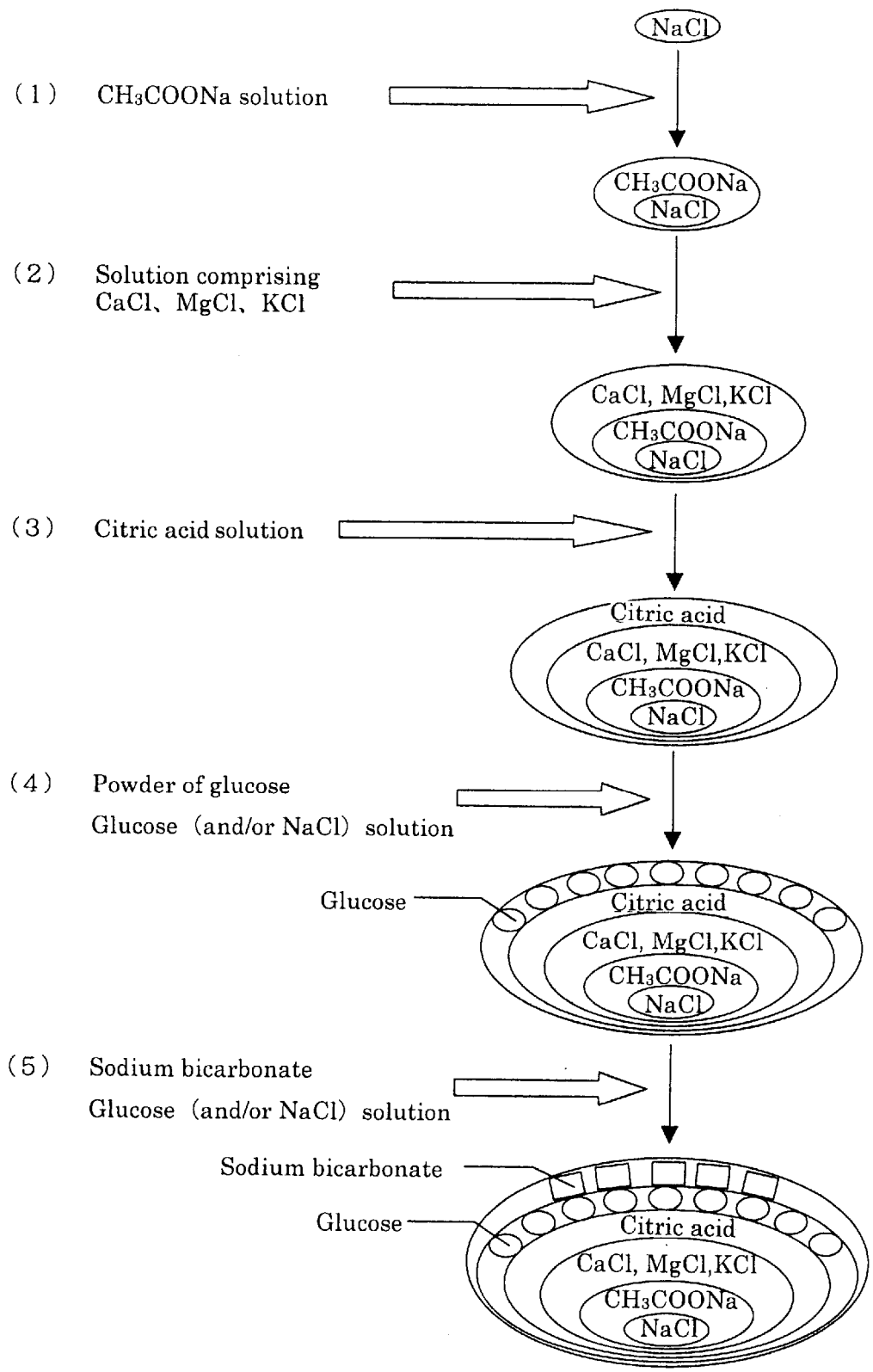
FIG. 1 is an illustration showing the process for producing the solid pharmaceutical preparation for dialysis according to the present invention.

The order of coating multiple layers in the present invention is not limited but certain layers are necessarily separated from each other in order for these layers not to contact each other directly. One of the methods for separating these layers preferably comprises providing an intermediate layer containing an electrolyte for hemodialysis excluding sodium acetate or glucose between the layers (A), (B) and (C). The layer (C) containing sodium bicarbonate is preferably provided as an outer layer and, preferably, the outermost layer of the preparation because it is feared that the outer layer may be decomposed by the heat or moisture added in the manufacturing process.

In the present invention, the nucleating particles consisting of sodium chloride are crystals with a particle diameter of about 0.1 to 1.0 mm and a water content of about 0 to 0.1%. The water content is expressed in terms of loss (%) in weight of said compound upon drying at 80° C. for 3 hours and does not include water of crystallization in said compound.

An electrolyte for hemodialysis in the present invention includes sodium chloride at least forming a nucleating particle, calcium chloride, magnesium chloride, potassium chloride, sodium acetate, and sodium bicarbonate, and may include other electrolytes such as potassium acetate, calcium gluconate, calcium citrate and the like. Said magnesium chloride includes magnesium chloride.$6H_2O$, etc, and said calcium chloride includes calcium chloride.$2H_2O$ or calcium chloride.$1H_2O$, etc. The sodium acetate includes sodium acetate anhydride, sodium acetate.$3H_2O$, etc.

The solid organic acid in the present invention includes pharmaceutically acceptable solid organic acids, for example, citric acid, oxalic acid, tartaric acid, maleic acid, ascorbic acid, oxaloacetic acid, isocitric acid, malic acid and the like. The organic acid is preferably, citric acid.

In the present invention, glucose is preferably in the form of powder with a particle diameter of about 0.01 to 0.5 mm and a water content of about 0 to 1%. For simplification of the granulation step, it is more preferably in the form of non-pulverized crystals with a particle diameter of 0.03 to 0.5 mm. Said glucose may contain another sugar ingredient, such as maltose, xylitol, trehalose, etc.

In the present invention, sodium bicarbonate is preferably in the form of powder with a particle diameter of about 0.01 to 0.5 mm and a water content of about 0 to 0.1%. For simplification of the granulation step, it is preferably in the form of non-pulverized crystals with a particle diameter of 0.03 to 0.5 mm.

The solid pharmaceutical preparation for dialysis according to the present invention is preferably a multi-layered particle consisting of a nucleating particle and 5 layers consisting of first to fifth layers on said nucleating particle. A group of preferable compounds forming each layer in said particles is as follows:

Nucleating particles: sodium chloride
First layer (layer A): sodium acetate
Second layer: calcium chloride, magnesium chloride, potassium chloride and sodium chloride
Third layer (layer B): solid organic acid
Fourth layer: glucose and sodium chloride
Fifth layer (layer C): sodium bicarbonate and sodium chlorides The solid pharmaceutical preparation for dialysis according to the present invention is a coated particle providing the layers (A), (B) and (C) separated respectively as described above, and it is thereby not only possible to prevent sodium bicarbonate and the solid organic acid, and sodium bicarbonate and the electrolyte, from being contacted with each other but is also possible to prevent the solid organic acid and sodium acetate from being contacted with each other.

In 1 kg of the solid pharmaceutical preparation for dialysis according to the present invention, e.g. the following ingredients are contained in the following amounts:

| | |
|---|---|
| Sodium chloride | 532 to 760 g |
| Sodium acetate | 15 to 98 g |
| Potassium chloride | 7 to 22 g |
| Calcium chloride ($2H_2O$) | 15 to 29 g |
| Magnesium chloride ($6H_2O$) | 5 to 20 g |
| Sodium bicarbonate | 168 to 336 g |
| Citric acid | 13 to 32 g |
| Glucose | 100 to 200 g. |

The solid pharmaceutical preparation for dialysis according to the present invention is dissolved in water to prepare a dialysis solution. The dialysis solution has, e.g., the following composition (final concentration):

| | |
|---|---|
| $Na^+$ | 130 to 150 mEq/L |
| $K^+$ | 1.0 to 3.0 mEq/L |
| $Ca^{2+}$ | 2.0 to 4.0 mEq/L |
| $Mg^{2+}$ | 0.5 to 2.0 mEq/L |
| $Cl^-$ | 100 to 125 mEq/L |
| $CH_3COO^-$ | 2 to 12 mEq/L |
| $HCO_3^-$ | 20 to 40 mEq/L |
| Citric acid | 2.0 to 5.0 mEq/L |
| Glucose | 100 to 200 mg/dL. |

The contents in the solid preparation for dialysis according to the present invention can be easily made uniform by dissolving the ingredients added in a small amount, that is, sodium acetate, potassium chloride, calcium chloride, magnesium chloride and the solid organic acid in water to form an aqueous solution to be used as coatings.

The other ingredients added in a large amount, that is, sodium chloride, glucose and sodium bicarbonate are used in the form of powder, nucleating particles or a coating layer whereby the granulation step is simplified. Glucose and sodium bicarbonate are used preferably in the form of non-pulverized crystalline powder.

The solid pharmaceutical preparation for dialysis according to the present invention can be produced by centrifugal fluid granulation, rotating granulation, fluidized-bed granulation or a combination thereof.

The solid pharmaceutical preparation for dialysis in the present invention is a coated particle providing the above layers (A), (B) and (C) respectively separated. It is manufactured by coating the layer (A) containing sodium acetate but not containing solid organic acid on the nucleating particles consisting of sodium chloride, coating a layer (B) containing solid organic acid but not containing sodium acetate on the layer (A) but separated from this layer (A), and then, coating a layer (C) containing solid bicarbonate on the layer (B) but separated from this layer (B).

Hereinafter, the process for producing the pharmaceutical preparation for dialysis according to the present invention is described by reference to the drawings.

FIG. 1 is an illustration showing the process for producing the pharmaceutical preparation for dialysis according to the present invention. The product obtained in each step is not limited to the form shown in FIG. 1.

(1) First, 900 to 1,400 g sodium chloride with a particle diameter of 0.1 to 1.0 mm serving as nucleating particles are introduced into a granulation drying unit for rotatively fluidizing. The particles are sprayed with 200 to 400 ml of an aqueous solution containing 60 to 130 g sodium acetate and then dried to form a first layer of 1 to 10 μm in thickness thereon. At least a part of the surface of the sodium chloride as nucleating particles is coated with said sodium acetate. The spraying method involves spraying the particles with the aqueous sodium acetate solution at a rate of 8 to 30 ml/min. for 7 to 50 minutes. The drying is preferably continued at 70 to 90° C. during the above spraying. The water content in the granulated product after drying is preferably 0.1 to 2.0%.

(2) The granulated product obtained in step (1) is sprayed with 80 to 250 ml of an aqueous solution containing 25 to 50 g calcium chloride, 15 to 30 g magnesium chloride and 10 to 40 g potassium chloride for 5 to 40 minutes at a rate of 7 to 15 ml/min. and then dried at 70 to 90° C. to form a second layer of 1 to 10 μm in thickness thereon. Sodium chloride as nucleating particles and sodium acetate contained in the first layer are coated with the second layer. For the purpose of separating sodium acetate contained in the first layer from the organic acid contained in the third layer and thickening the second layer, said aqueous solution may contain sodium chloride. Further, the second layer may be made of plural layers by spraying the particles with an aqueous solution containing calcium chloride and magnesium chloride, drying the particles, spraying the particles with an aqueous solution containing potassium chloride and drying the particles. The water content in the granulated product after drying is preferably 0.1 to 2.0%.

(3) The granulated product obtained in step (2) is sprayed with 40 to 150 ml aqueous solution containing 20 to 50 g solid organic acid for 3 to 30 minutes at a rate of 4 to 10 ml/min. and then dried at 70 to 90° C. to form a third layer of 1 to 5 μm in thickness thereon. The various electrolytes contained in the second layer are coated with the third layer. The water content in the granulated product after drying is preferably 0.1 to 2%.

(4) 130 to 300 g glucose powder with a particle diameter of 0.03 to 0.5 mm is introduced into, and mixed with, the granulated product obtained in step (3), and then the mixture is sprayed with 50 to 150 ml of an aqueous solution containing 2 to 20 g glucose for 5 to 30 minutes at a rate of 5 to 10 ml/min. and then dried at 60 to 80° C. whereby the glucose powder is allowed to adhere to the surface of the product to form a fourth layer thereon. Although the thickness of the fourth layer is not uniform, the solid organic acid is coated with the aqueous solution containing glucose. To improve adhesion of the glucose powder to the product said aqueous solution may contain sodium chloride. The water content in the granulated product after drying is preferably 0.1 to 2%.

(5) 350 to 600 g sodium bicarbonate powder with a particle diameter of 0.03 to 0.5 mm is introduced into, and mixed with, the granulated product obtained in step (4), and the mixture is sprayed with 50 to 250 ml aqueous solution containing 4 to 40 g glucose for 5 to 50 minutes at a rate of 5 to 10 ml/min. and then dried at 50 to 70° C. thereby allowing the sodium bicarbonate powder to adhere to the surface of the product to form a fifth layer. Although the thickness of the fifth layer is not uniform, the sodium bicarbonate is coated with the aqueous solution containing glucose. The water content in the product after drying is preferably 0.1 to 2%. After the fifth layer is formed, the particles are dried at 50 to 70° C. for 3 to 30 minutes whereby a solid pharmaceutical preparation for dialysis is obtained as the final granulated product. The solid pharmaceutical preparation for dialysis has a particle diameter of 0.2 to 2 mm with a water content of 0.1 to 0.5%.

EXAMPLES

Hereinafter, the present invention is described in more detail by reference to the following examples, which however are not intended to limit the present invention.

Example 1

Figure 2:
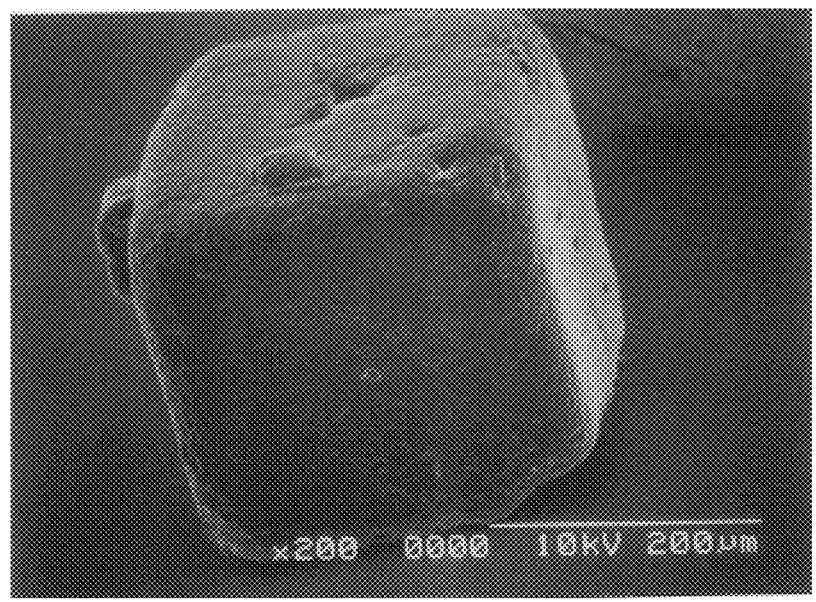
FIG. 2 is an electron micrograph (×200) of a cubic crystalline particle of sodium chloride.
Figure 3:
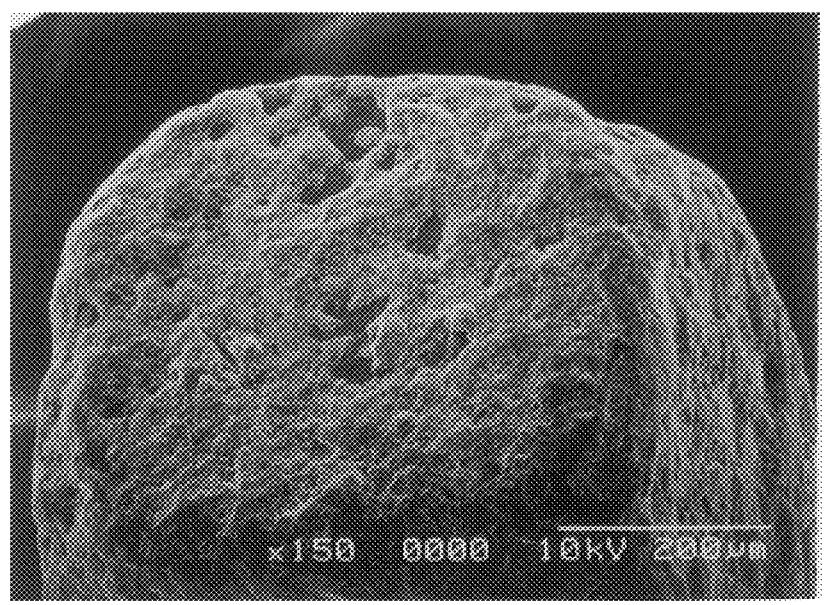
FIG. 3 is an electron micrograph (×150) of a particle of sodium chloride obtained by spraying the particle with an aqueous sodium acetate solution and drying it.
Figure 4:
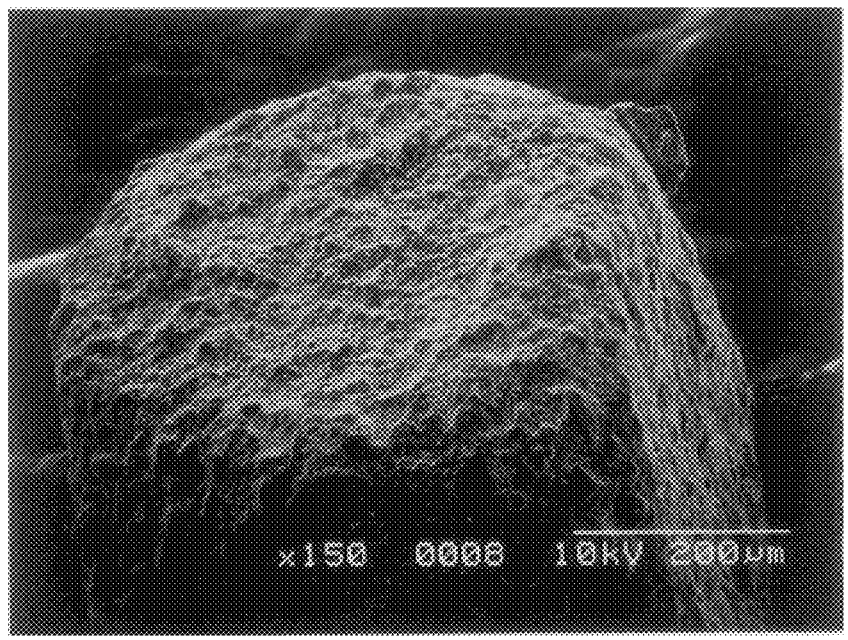
FIG. 4 is an electron micrograph (×150) of a particle obtained by spraying the surface of the particle shown in FIG. 3 with an aqueous mixture of calcium chloride, magnesium chloride and potassium chloride, and then drying it.
Figure 5:
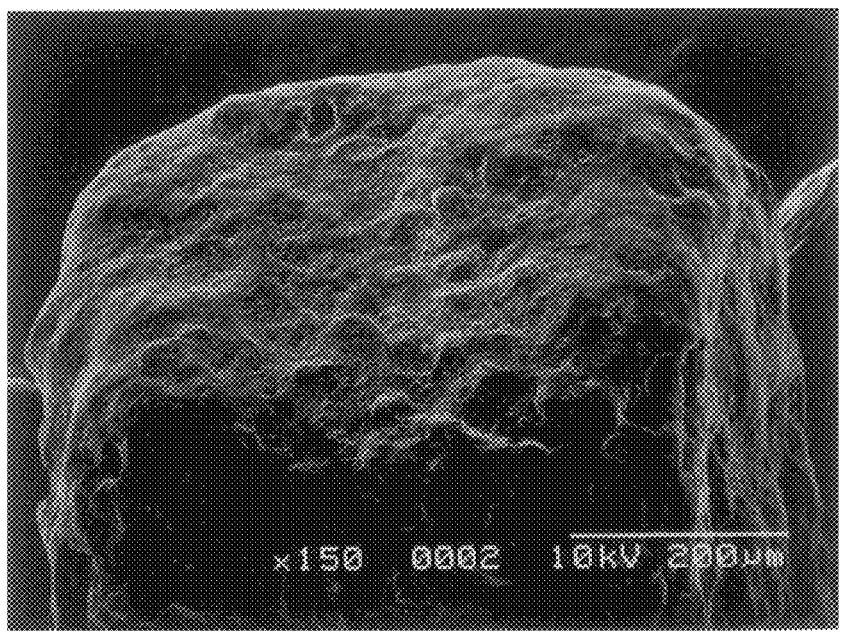
FIG. 5 is an electron micrograph (×150) of a particle obtained by spraying the surface of the particle shown in FIG. 4 with an aqueous solution of citric acid, and then drying it.
Figure 6:
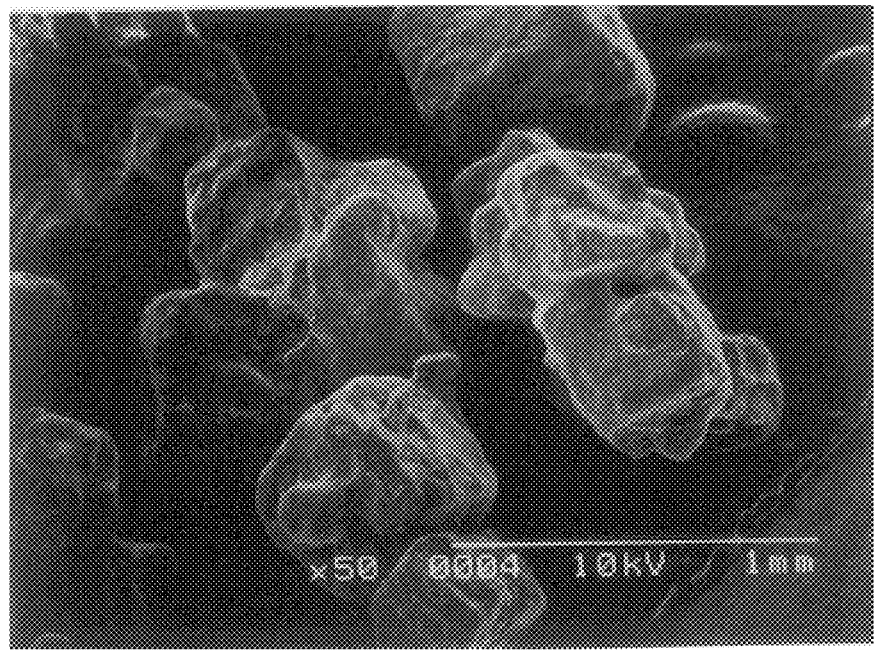
FIG. 6 is an electron micrograph (×50) of a particle obtained by mixing glucose powder with the particle shown in FIG. 5, spraying it with an aqueous solution containing glucose and sodium chloride, and drying it.
Figure 7:
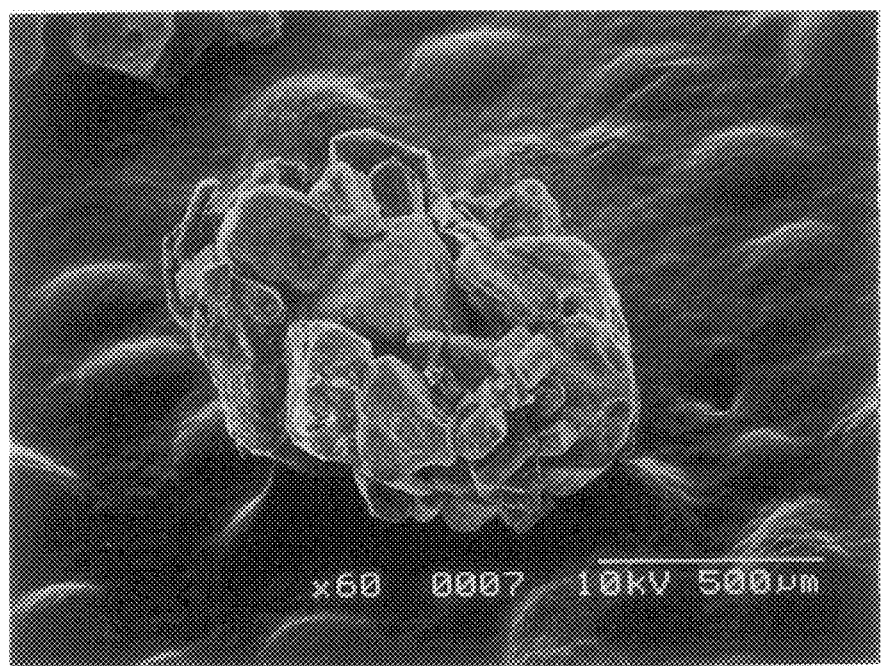
FIG. 7 is an electron micrograph (×50) of a particle obtained by mixing sodium bicarbonate powder with the particle shown in FIG. 6, spraying it with an aqueous solution containing glucose and sodium chloride, and drying it.
Figure 8:
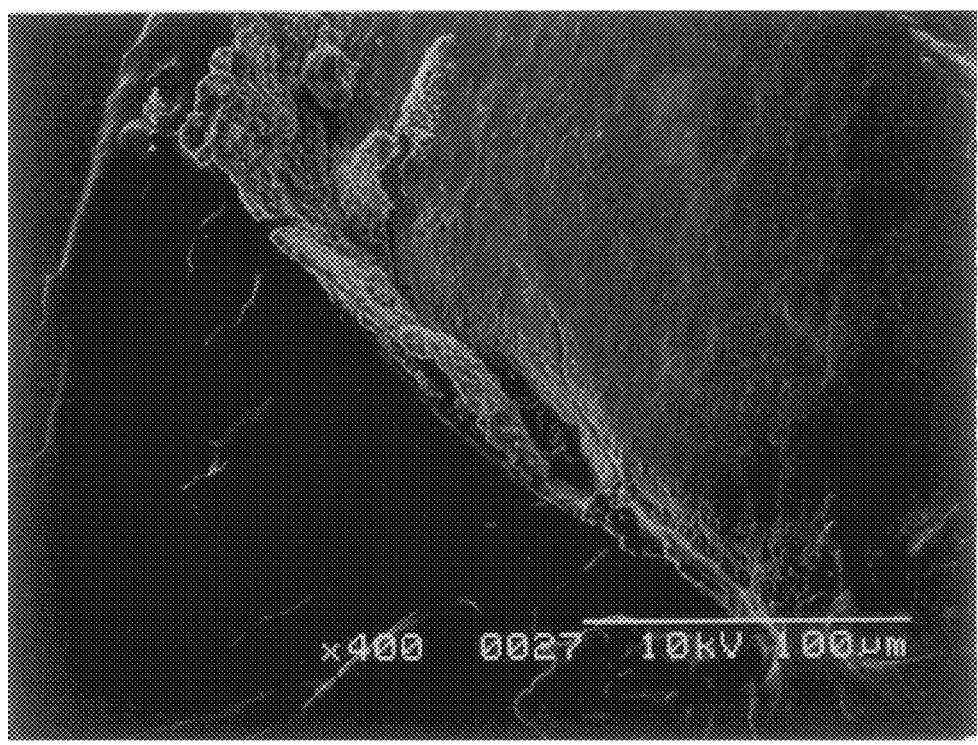
FIG. 8 is an electron micrograph (×400) of a part of a section of the particle shown in FIG. 7.

1,282 g sodium chloride with an average particle diameter of 0.4 mm was introduced as nucleating particles into a granulation drying unit for rotatively fluidizing (Multiplex MP-01 model, manufactured by Powrex) and sprayed for 20 minutes with a total of 350 ml of an aqueous solution containing 104 g sodium acetate at a spraying temperature of 80° C. and simultaneously dried to form a first layer thereon. An equant (or cubic) particle of sodium chloride is shown in FIG. 2, and a particle having the first layer formed on the surface of the sodium chloride particle is shown in FIG. 3. Then, the particles were sprayed for 15 minutes with a total of 150 ml of an aqueous solution containing 42 g calcium chloride, 23 g magnesium chloride and 34 g potassium chloride at a spraying temperature of 80° C. and simultaneously dried to form a second layer thereon. A particle having the second layer formed thereon is shown in FIG. 4. Further, these particles were sprayed for 15 minutes with a total of 70 ml of an aqueous solution containing 34 g citric acid at a spraying temperature of 80° C. and simultaneously dried to form a third layer thereon. A particle having the third layer formed thereon is shown in FIG. 5. 165 g glucose powder with a particle diameter of 0.07 to 0.4 mm was introduced into, and mixed with, the particles which were then sprayed for 8 minutes with a total of 50 ml of an aqueous solution containing 10 g glucose and 20 g sodium chloride at a spraying temperature of 60° C. and simultaneously dried to form a fourth layer thereon. A particle having the fourth layer formed thereon is shown in FIG. 6. Then, 544 g sodium bicarbonate powder with a particle diameter of 0.05 to 0.2 mm was introduced into, and mixed with, the particles which were then sprayed for 15 minutes with a total of 100 ml of an aqueous solution containing 20 g glucose and 20 g sodium chloride at a spraying temperature of 60° C. and simultaneously dried to form a fifth layer thereon. Thereafter, the particles were further dried at 60° C. for 15 minutes to give a solid pharmaceutical preparation for dialysis with an average particle diameter of 0.8 mm as a final granulated product. The solid pharmaceutical preparation for dialysis as the final granulated product is shown in FIG. 7, and a section of the pharmaceutical preparation for dialysis is shown in FIG. 8.

From 2,200 g of the resulting solid pharmaceutical preparation for dialysis, 52.5 g was taken thrice arbitrarily and each batch of the preparation was dissolved in water to prepare 5 L of a dialysis solution. The contents of the respective ingredients in each dialysis solution were measured. The results are shown in Table 1. $Na^+$ and $K^+$ were determined by flame spectrometry, $Ca^{2+}$ and $Mg^{2+}$ by atomic absorption photometry, $Cl^-$ by titration with silver nitrate, $CH_3COO^-$, citric acid and glucose by liquid chromatography, and $HCO_3^-$ by ion chromatography.

TABLE 1

|  | $Na^+$ | $K^+$ | $Ca^{2+}$ | $Mg^{2+}$ | $Cl^-$ | $CH_3COO^-$ | $HCO_3^-$ | Citric acid | Glucose |
|---|---|---|---|---|---|---|---|---|---|
| First time | 141.2 | 1.97 | 2.53 | 1.01 | 113.6 | 5.52 | 27.5 | 2.43 | 90 |
| Second time | 139.1 | 1.92 | 2.42 | 0.99 | 110.2 | 5.29 | 29.6 | 2.52 | 97 |
| Third time | 140.3 | 1.95 | 2.46 | 1.02 | 112.4 | 5.38 | 28 | 2.35 | 94 |
| Mean | 140.2 | 1.95 | 2.47 | 1.01 | 112.1 | 5.40 | 28.4 | 2.43 | 94 |
| Standard deviation | 0.9 | 0.02 | 0.05 | 0.01 | 1.4 | 0.09 | 0.9 | 0.07 | 3 |

Units: Glucose, mg/dL; others, $mEq/L_3$

As is evident from Table 1, the solid pharmaceutical preparation for dialysis according to the present invention was excellent in the uniformity of the respective ingredients with a standard deviation of 1.4 or less.

Further, from 2,200 g of the resulting solid pharmaceutical preparation for dialysis, 52.5 g was taken arbitrarily and introduced into an aluminum laminated bag having gas barrier properties (thickness, 104 μm; outer layer, polyethylene terephthalate (12 μm); intermediate layer, aluminum (12 μm); inner layer, linear low-density polyethylene (80 μm)) and stored at 40° C. for 3 months. Comparison after this storage indicated that, as compared with the solid pharmaceutical preparation for dialysis before storage, there was neither change in the contents of the ingredients nor coloration thereof.

Further, the solid pharmaceutical preparation for dialysis after storage for 3 months was dissolved in reverse-osmotic water to prepare 5 L of a dialysis solution, and separately 52.5 g of the solid pharmaceutical preparation for dialysis before storage was dissolved in reverse-osmotic water to prepare a dialysis solution. Comparison therebetween indicated that there was neither coloration in the solution nor change in the pH value.

Effect of the Invention

The solid pharmaceutical preparation for dialysis according to the present invention is a coated granule, particle or powder consisting of nucleating particles made of sodium chloride and 5 layers consisting of first to fifth layers on said nucleating particles, thereby making it possible to prevent generation of carbon dioxide by reaction of sodium bicarbonate with a solid organic acid, formation of carbonates by reaction of sodium bicarbonate with electrolytes and formation of acetic acid by reaction of a solid organic acid with sodium acetate.

Further, glucose and sodium bicarbonate are used as coatings in the form of non-pulverized crystals whereby the step of pulverizing glucose and sodium bicarbonate can be omitted thereby simplifying the step of granulating the solid pharmaceutical preparation for dialysis.

Further, in the process for producing the solid pharmaceutical preparation for dialysis according to the present invention, the ingredients added in a large amount, such as sodium chloride, glucose and sodium bicarbonate are used in the form of powder while the ingredients in a small amount, such as potassium chloride, calcium chloride, magnesium chloride, sodium acetate and a solid organic acid are dissolved in water to be used as aqueous solutions for coating, thereby achieving not only uniformity of the ingredients in the solid pharmaceutical preparation for dialysis but also simplification of the granulation step.

What is claimed is:

1. A solid pharmaceutical preparation for dialysis comprising an electrolyte for hemodialysis, a solid organic acid and glucose and being in the form of a plurality of layers on the surface of a nucleating particle of sodium chloride, wherein the plurality of layers consist essentially of, the following layers in the following order, a layer (A) comprising sodium acetate but not containing the solid organic acid, a layer (B) comprising the solid organic acid but not containing sodium acetate, and a layer (C) comprising sodium bicarbonate, said layers (A), (B) and (C) being separated from each other such that layer (B) does not contact layer (A) and layer (C) does not contact layer (B).

2. The solid pharmaceutical preparation for dialysis according to claim 1, wherein layer (C) is an outermost layer.

3. The solid pharmaceutical preparation for dialysis according to claim 1, wherein the electrolyte for hemodialysis comprises sodium chloride, calcium chloride, magnesium chloride, potassium chloride, sodium acetate and sodium bicarbonate.

4. The solid pharmaceutical preparation for dialysis according to claim 1, wherein the solid organic acid is one or more acids selected from the group consisting of citric acid, oxalic acid, tartaric acid, maleic acid, ascorbic acid, oxaloacetic acid, isocitric acid and malic acid.

5. A solid pharmaceutical preparation for dialysis according to claim 1, which comprises a nucleating particle consisting of sodium chloride and, in order, a first layer (A) on said nucleating particle and containing sodium acetate but not containing a solid organic acid, a second layer containing at least one ingredient selected from the group consisting of calcium chloride, magnesium chloride, potassium chloride and sodium chloride but not containing sodium acetate and not containing a solid organic acid, a third layer (B) containing a solid organic acid but not containing sodium acetate, a fourth layer containing glucose powder and a fifth layer (C) containing sodium bicarbonate powder.

6. The solid pharmaceutical preparation for dialysis according to claim 5, wherein the glucose powder and sodium bicarbonate powder are in the form of non-pulverized crystals.

7. The pharmaceutical preparation for dialysis according to claim 5, wherein the glucose powder and sodium bicarbonate powder are each in the form of crystalline powder with a particle diameter of 0.03 to 0.5 mm.

8. The pharmaceutical preparation according to claim 1, wherein the solid organic acid is citric acid.

9. A process for producing a pharmaceutical preparation for dialysis, comprising:
   (a) spraying an aqueous solution containing sodium acetate but not containing a solid organic acid on the surface of nucleating particles consisting of sodium chloride, and drying the particles,
   (b) spraying the particles obtained in step (a) with an aqueous solution containing at least one ingredient selected from the group consisting of calcium chloride, magnesium chloride, potassium chloride and sodium chloride but not containing sodium acetate and not containing a solid organic acid, and drying the particles,
   (c) spraying the particles obtained in step (b) with an aqueous solution containing a solid organic acid and not containing sodium acetate and drying the particles,
   (d) mixing glucose powder with the particles obtained in step (c), then spraying the particles with an aqueous solution containing glucose and/or sodium chloride and drying the particles, and
   (e) mixing sodium bicarbonate powder with the particles obtained in step (d), then spraying the particles with an aqueous solution containing glucose and/or sodium chloride and drying the particles.

10. The process for producing a solid pharmaceutical preparation for dialysis according to claim 9, wherein the glucose powder and sodium bicarbonate powder are in the form of non-pulverized crystals.

11. The process for producing a solid pharmaceutical preparation for dialysis according to claim 9, wherein the glucose powder and sodium bicarbonate powder are in the form of crystals with a particle diameter of 0.03 to 0.5 mm.

12. The process for producing a solid pharmaceutical preparation for dialysis according to claim 9, wherein the solid organic acid is citric acid.

* * * * *